US008658190B2

(12) United States Patent
Miner

(10) Patent No.: US 8,658,190 B2

(45) Date of Patent: Feb. 25, 2014

(54) ENHANCED TUBURCULOCIDAL ACTIVITY AND DECREASED FUMES FROM GLUTARALDEHYDE DISINFECTANT USING ACETATE SALTS AND ALCOHOL

(75) Inventor: Norman A. Miner, Arlington, TX (US)

(73) Assignee: DFB Technology, Ltd., Fort Worth, TX (US)

( * ) Notice: Subject to any disclaimer, the term of this patent is extended or adjusted under 35 U.S.C. 154(b) by 1476 days.

(21) Appl. No.: 11/178,806

(22) Filed: Jul. 11, 2005

(65) Prior Publication Data

US 2007/0010586 A1 Jan. 11, 2007

(51) Int. Cl.
*A61K 31/11* (2006.01)
*A01N 25/02* (2006.01)

(52) U.S. Cl.
USPC ........... 424/405; 514/693; 514/705; 510/161; 510/382

(58) Field of Classification Search
USPC ............ 514/693, 705; 510/161, 382; 424/405
See application file for complete search history.

(56) References Cited

U.S. PATENT DOCUMENTS

| | | | | |
|---|---|---|---|---|
| 3,016,328 | A | 1/1962 | Pepper et al. | |
| 3,282,775 | A | 11/1966 | Stonehill | |
| 3,697,222 | A | 10/1972 | Gonzalo | |
| 3,912,809 | A | 10/1975 | Rendon | |
| 3,917,850 | A | 11/1975 | Boucher | |
| 3,983,252 | A | 9/1976 | Buchalter | |
| 4,093,744 | A | 6/1978 | Winicov et al. | |
| 4,103,001 | A | 7/1978 | Schattner | |
| 4,436,754 | A | 3/1984 | Jacobs | |
| 4,469,614 | A | 9/1984 | Martin | |
| 4,804,685 | A | 2/1989 | Jacobs | |
| 4,851,449 | A | 7/1989 | Bruckner et al. | |
| 5,322,856 | A | 6/1994 | Martin | 514/574 |
| 5,348,678 | A | 9/1994 | Hodam, Jr. et al. | |
| 5,674,829 | A | 10/1997 | Martin | |
| 5,863,547 | A | 1/1999 | Miner | |
| 6,040,283 | A * | 3/2000 | Miner | 510/161 |
| 2004/0242702 | A1 | 12/2004 | Martin | |

FOREIGN PATENT DOCUMENTS

| | | |
|---|---|---|
| EP | 251743 | 1/1988 |
| EP | 279704 | 8/1988 |
| WO | WO 03/011027 | 2/2003 |

OTHER PUBLICATIONS

Sigma Aldrich Biological Buffers information sheet, pp. 1-11 Copyrights 2008 http://www.sigmaaldrich.com/Area_of_Interest/Biochemicals/BioUltra/Biological_Buffers.html accessed Aug. 7, 2008.*

Harris Exploring Chemical Analysis, 2nd Ed. © 2001, W.H.Freeman and Company, pp. 19-26, Editor, Jessica Fiorillo.*

Pepper, Rollin E., et al., "Sporicidal Activity of Alkaline Alcoholic Saturated Dialdehyde Solutions" *Department of Microbiology, Ethicon, Inc.*, Somerville, NJ, Mar. 13, 1963; pp. 384-388.

Robinson, Richard A., et al. "Culture Variability Associated with the U.S. Environmental Protection Agency Tuberculocidal Activity Test Method", *Department of Microbiology and Department of Statisticsm Brigham Young University*, May 15, 1966; vol. 62, No. 8, pp. 2681-2686.

Scott, Ph.D., Eileen M., et al. "Sterilization with Glutaraldehyde" pp. 65-88 Edition of block, 1980 or later.

Office Communication, issued in Korean Patent Application No. 10-2008-7003311, dated Nov. 30, 2010.

Office Communication issued in Canadian Patent Application No. 2,614,728, dated Jul. 13, 2011.

* cited by examiner

*Primary Examiner* — Kortney L Klinkel

(74) *Attorney, Agent, or Firm* — Fulbright & Jaworski LLP

(57) ABSTRACT

The addition of alcohol plus acetate salts unexpectedly enhanced the tuberculocidal activity of glutaraldehyde, and decreased the fumes of glutaraldehyde from the formula of a high-level disinfectant.

11 Claims, No Drawings

ENHANCED TUBURCULOCIDAL ACTIVITY AND DECREASED FUMES FROM GLUTARALDEHYDE DISINFECTANT USING ACETATE SALTS AND ALCOHOL

FIELD OF THE INVENTION

This invention is an improvement over my U.S. Pat. No. 5,863,547 dated Jan. 26, 1999. It newly discovers that the addition of both alcohol and acetate salts are necessary for a glutaraldehyde high-level disinfectant to kill mycobacteria (TB), Gram-positive and Gram-negative vegetative bacteria, fungi, and viruses within 10 min at 20 C. Furthermore the fumes of glutaraldehyde are significantly suppressed by the alcohol and acetate salts combination. As a result, more rapid kill and less fumes are achieved for an improved glutaraldehyde-based formulation for the high-level disinfection and/or sterilization of heat-sensitive medical, dental, and veterinary reusable devices. The disclosure of my previous U.S. Pat. No. 5,863,547 of Jan. 26, 1999 is incorporated by reference.

BACKGROUND OF THE INVENTION

Many medical devices are constructed of heat-sensitive polymeric materials, glues, glass lenses, and electronic components. Examples of such devices are gastroscopes, colonoscopes, cystoscopes, arthroscopes, transesophageal and vaginal probes, and anesthesia and respiratory therapy equipment. These heat-sensitive devices are very expensive, and thus are typically reused from one patient to another, and cannot be sterilized by steam or dry heat. These heat-sensitive devices are therefore disinfected with the highest levels of liquid chemical disinfectants. High-level disinfectants are able to kill Gram-positive and Gram-negative vegetative bacteria, mycobacteria such as *Mycobacterium tuberculosis*, fungi, and all types of viruses, with a relatively short exposure, and can also kill high numbers of bacterial spores dried onto surfaces with a much longer exposure time.

The high-level disinfectant chemistries that are available for disinfecting medical devices are glutaraldehydes, other aldehydes such as ortho-phthalaldehyde and formaldehyde, peracetic acid, hypochlorous acid, and chlorine dioxide. These chemistries all have serious limitations as high-level disinfectants. Glutaraldehyde requires about 45 min at 25 C to kill 6 log 10 of mycobacteria, and about 10.0 hrs at 25 C to kill bacterial spores as measured by the Association of Official Analytical Chemists (AOAC) Sporicidal Test 966.04. These are impractical exposure times and temperatures that are often arbitrarily decreased in practice. Glutaraldehyde has a serious odor and sensitization problem that requires special equipment for fume containment and exhaustion. Formaldehyde is a known carcinogen with a noxious odor. Ortho-phthaladehyde has vapors that are relatively odorless, but the vapors can sensitize patients and staff. Some patients and staff have become sensitized to ortho-phthaladehyde, and reacted with anaphylactic shock to repeated exposure to fumes they could not smell. Ortho-phthaladehyde requires about 32 hrs to kill bacterial spores in the AOAC Sporicidal Test 966.04. Ortho-phthaldehyde is relatively insoluble, and thus difficult to rinse from surfaces. The aldehydes may be used and reused for typically 14 to 30 days. Peracetic acid has a sharp odor that must be contained within a machine, and the product is used with a temperature of 50 C to 56 C. The combination of the oxidative peracetic acid used at the relatively high temperature of 50 C to 56 C can be damaging to some glues and polymeric materials. All of the oxidative chemistries such as peracetic acid, hypochlorous acid, and chlorine dioxide are unstable and thus are single- or day-use products.

Thus there is a need for a high-level disinfectant that can disinfect within a practical exposure time and at ambient temperature, with a safe and detectable odor, and with an affordable period of use and reuse for many days. Towards that end my prior U.S. patent was a first step improvement.

Previously we discovered that relatively low concentrations of alcohol enhanced the mycobactericidal activity of glutaraldehyde (U.S. Pat. No. 5,863,547). This patent, however, taught specifically to avoid acetate salt additions (column 2, lines 28-30). Further studies have now discovered that acetate salts in combination with alcohol are necessary to optimize the mycobactericidal activity of glutaraldehyde for a very quick and practical exposure time and temperature such as 10.0 min at 20 C. A further surprising discovery was that the fumes of glutaraldehyde were greatly reduced by the presence of alcohol and acetate salts at the appropriate levels.

With the addition of acetate salts, the pH-value of the un-activated glutaraldehyde solution increased to about 6.5 The stable pH-value for glutaraldehyde is about pH 3.5 to 4.5. Because of the pH-value of 6.5, the glutaraldehyde concentration of the un-activated formulation slowly decreased over a period of about 9 to 12 months of warehouse storage. Thus for example it was necessary to start with a glutaraldehyde concentration of about 3.5% in order to have a glutaraldehyde concentration of at least 2.0% after 12 months of storage, followed by 14 days of use and reuse. Repeated use of the disinfectant inadvertently dilutes the glutaraldehyde concentration as freshly cleaned wet devices carry some water into the disinfectant, and freshly disinfected devices carry some glutaraldehyde to be rinsed away. Also, because of the inadvertent dilution that occurs during 14 days of use and re-use, it is necessary to start with somewhat higher, i.e., up to about 26% alcohol in order to have about 15% alcohol after the inadvertent dilution caused by use and re-use. The acetate salts also must start at the higher concentration of about 8% in order to maintain a minimum effective concentration of about 5% after use and re-use for 14 days. Effective concentration as used here means concentration after about 14 days of use and re-use.

It is a primary objective of the present invention to improve on the formulation of my own prior U.S. Pat. No. 5,863,547 in several important ways. First, to increase the rate of antimicrobial kill; second, to modify the formulation so that it maintains a minimum effective concentration even after use and re-use, for example for 14 days; third, to enhance the rate of kill and the effectiveness of disinfectant by adding acetate salts at levels of from 3% to 8%; and fourth, by surprisingly decreasing the acrid odor of glutaraldehyde fumes by combination of the acetate salts present and the alcohol that is present.

The method or manner of achieving this primary objective as well as others will become apparent from the following description of the invention.

BRIEF SUMMARY OF THE INVENTION

This invention describes a high-level disinfectant formulation that can disinfect heat-sensitive medical devices quickly, for example within 10.0 min at ambient temperature, and as well has detectable, but relatively low, fumes of glutaraldehyde. The formula contains glutaraldehyde (2.0% to 5.0%), plus alcohol (5% to 26%), plus acetate salts (3% by weight to 8% by weight), all buffered at the time of use with an alkaline buffer system to pH-value 7.3 to 7.9. This stabilizes the glutaraldehyde over a 14-day period of use and reuse. The worstcase concentrations of this formula can kill bacterial spores as measured by the AOAC Sporicidal Test 966.04 within 6.0 hrs at 20 C. The fumes of glutaraldehyde are reduced as much as 75%, not from the reduction of the concentration of glutaraldehyde, but rather due to the presence of the alcohol and the acetate salts. These discoveries provide an improved high-level disinfectant formulation with a practical exposure time and temperature.

DETAILED DESCRIPTION OF A PREFERRED EMBODIMENT

Glutaraldehyde is the first ingredient of the composition and may be present in the initial amount of between about 2.0% and 5.0% by volume. Unless specified otherwise the ranges of percent herein expressed are by volume. Preferably the starting concentration of the glutaraldehyde is 3.5% by volume so that the glutaraldehyde concentration can remain at or above 2.0% during storage and use and re-use for 14 days. The acetate salts will increase the storage pH value of the formulation to about 6.5. Glutaraldehyde is most stable at a pH value of about 3.5 to 4.5. During warehouse storage over a period of about 12 months at pH 6.5, the glutaraldehyde concentration will gradually decrease. Thus it is necessary to start with the higher concentration of glutaraldehyde to maintain effective minimum concentrations after warehouse storage and 14 days of use and re-use. Glutaraldehyde provides the primary antimicrobial activity of the composition.

Alcohol is the second ingredient of the composition. Appropriate alcohols for use in the present invention are straight and branched chain water miscible alcohols, including methanol, ethanol, and isopropranol, as well as others. Isopropanol and ethanol are preferred.

The alcohol is present in a concentration of between about 5% to about 26% by volume. The preferred alcohol concentration is 24-26% by volume. This alcohol concentration greatly enhances the tuberculocidal activity of for example to 2.0% glutaraldehyde. Alcohol alone is not tuberculocidal at 5% to 20% by volume, nor is 2.0% glutaraldehyde tuberculocidal at 20° C. within a practical exposure time of 10 min. However, 5.0% to 26% by volume alcohol in combination with for example 2.0% glutaraldehyde is rapidly tuberculocidal within 10 min. at 20° C. Further enhancement of the tuberculocidal activity of glutaraldehyde with acetate allows the concentration of glutaraldehyde in the formula to be lowered.

Isopropyl alcohol is the preferred second ingredient of the composition, and may be present in the preferred initial amount of between 24% and 26% by volume. The isopropyl alcohol will remain stable during warehouse storage. When the disinfectant is used and re-used for 14 days, some alcohol will evaporate, and some alcohol will be inadvertently diluted as wet equipment carries water into the disinfectant, and the freshly disinfected equipment will carry alcohol to be rinsed away. It is therefore necessary to start with for example about 26% initial volume of alcohol in order to have at least 15% alcohol after 14 days of use and re-use of the disinfectant. The preferred isopropyl alcohol in combination with acetate salts greatly enhances the tuberculocidal activity of glutaraldehyde and the alcohol also suppresses the foaming of the composition, as would otherwise occur from the added surfactant.

Acetate salts, preferably potassium or sodium acetate salts are the third ingredient of the composition, and may be present initially at about 3% by weight to 8% by weight The acetate salts are stable during warehouse storage. It is necessary to start with about 8% acetate salts by weight in order to have at least 5%, the preferred minimum effective level after use and re-use of the disinfectant for 14 days. The acetate salts in combination with the alcohol greatly enhance the tuberculocidal activity of the glutaraldehyde. The acetate salts also enhance the sporicidal activity of the composition. The acetate salts plus the alcohol surprisingly also suppress the fumes of glutaraldehyde which is of course desirable.

A buffer, preferably phosphate buffer, is the fourth ingredient of this disinfectant formulation. Glutaraldehyde is stable in this composition buffered to about pH 7.3 to 7.9 for about 14 days during use and re-use. Buffers other than phosphate salts cause about a 40% decrease in the glutaraldehyde concentration of disinfectants activated with, for example, bicarbonate buffers. As a result, phosphate is preferred. It is of value to the composition to have the activated glutaraldehyde concentration remain stable during 14 days of use and re-use. This chemical stability during the 14 days of use and re-use provides more glutaraldehyde for antimicrobial activity at any given time than if the composition had been buffered with another buffer. The amount of buffer is from 4 g/liter to 7 g/liter.

In the preferred composition, as in the composition of my previous patent, there is a surfactant. The preferred surfactant levels are 0.0025% by weight to 0.01% by weight. Suitable surfactant is not critical and basically the same surfactants may be used as are listed in my prior patent which is incorporated herein by reference.

Taken altogether, this combination of glutaraldehyde at 2% to 5%, alcohol at 5% to 26%, acetate salts at 3% by weight to 8% by weight, a low-foaming, non-ionic surfactant at 0.0025% to 0.01% by weight activated with a phosphate buffer, provides a high-level disinfectant that kills all non-spore-forming microbes within 10.0 min at ambient temperature, kills bacterial spores dried onto surfaces with their culture medium within 6.0 hrs at ambient temperature, has a non-offensive, yet noticeable and thus safely avoided, odor, and can be used safely and economically with heat-sensitive equipment for up to 14 days. It therefore accomplishes the invention objectives.

The following examples are offered to further illustrate but not necessarily limit the invention. It goes without saying that modifications both to the ingredients and the ranges of additions of the ingredients may be made without department from the spirit and scope of the invention. Put another way, the examples are illustrative but non-limiting of the scope of the invention.

Example 1

A typical formulation of this invention was mixed and is as follows:

| | |
|---|---|
| Glutaraldehyde | to 3.2% by volume |
| Isopropanol | 26% by volume |
| Non-ionic surfactant | .01% by weight |
| Na2HPO4 buffer | 7.4 pH |
| Acetate | 8% by weight |
| Water | remainder |

This formulation was used in Example 2.

Example 2

This example demonstrates that both the alcohol, preferably isopropanol, and the acetate salts are necessary for optimum tuberculocidal activity.

In this study, various formulas were prepared with and without the active ingredients isopropanol and potassium acetate and tested for the ability to kill *Mycobacterium bovis* var. BCG in a rate of kill suspension test. Five (5.0) ml of *M. bovis* var. GCG culture containing 5% (v/v) heat-inactivated calf serum were added to 45.0 ml of an Example 1 formulation at 20° C. After 2.5, 5.0, 7.5, and 10.0 minutes at 20° C., 1.0 ml of the reaction mixture was removed and serial ten-fold dilutions were made into 9 ml of neutralizing recovery medium. The dilutions were filtered through 0.45 p. membrane filters and rinsed with sterile deionized water. The filters were placed onto M7H9 agar in petri plates and incubated for 3-4 weeks at 35+2° C. Colonies were counted and multiplied by appropriate dilution factors to determine the number of surviving colony forming units (CFU) in the reaction flask at a given exposure. CIDEX®, a commercially available material was tested in the same manner with exposure times of 5.0, 10.0, 20.0, and 30.0 minutes at 25° C.

In both studies, the invention formulation containing 2.4% glutaraldehyde, 15% isopropanol, and 5% potassium acetate, killed *M. bovis* var. BCG faster than all other formulas including CIDEX®. The same formula diluted 1.5-fold to approximately 1.6% glutaraldehyde, 10% isopropanol, and 3.33% potassium acetate had the second fastest kill of *M. bovis* var. BCG. The formula containing 2.4% glutaraldehyde and 15% isopropanol (no potassium acetate) killed *M. bovis* var. BCG slightly faster than the formula containing 2.4% glutaraldehyde and 5% potassium acetate (no isopropanol) and CIDEX®.

In both studies, the invention formulas (full-strength and diluted 1.5-fold) containing both isopropanol and potassium acetate performed better than the formulas lacking one of these ingredients and performed better than CIDEX®. It therefore can be seen that isopropanol and potassium acetate are both necessary ingredients to greatly enhance the kill of *M. bovis* var. BCG.

The procedure necessary to reach the above conclusions in this example 2 were as follows:

Preparation of *Mycobacterium bovis* var. BCG

Fresh *Mycobacterium bovis* var. BCG was obtained within twelve months of this test. Cultures of *M. bovis* var. BCG were grown on M7H9 agar slants in 25×250 mm screw-capped test tubes for 21 to 25 days at 35±2° C. These were stock cultures and were stored in the refrigerator at 3±2° C. for use in a test. A broth culture was mixed on a vortex mixer and homogenized in a 40 ml tissue homogenizer using 5 to 10 strokes. One (1) part heat-inactivated calf serum was added to 19 parts of culture (a final concentration of 5% (v/v)).

Preparation of Invention Formulas

The following formulas were prepared and tested:

(1) 2.4% glutaraldehyde, 15% isopropanol, 5% potassium acetate, 0.001% keyacid blue, 0.0025% Laureth-23, Q.S. to 100 ml distilled water. Activate with Yellow #5, $NaH_2PO_4$ and $Na_2HPO_4$ to adjust pH to approximately 7.60.

(2) 2.4% glutaraldehyde, 15% isopropanol, 0.001% keyacid blue, 0.0025% Laureth-23, Q.S. to 100 ml distilled water (no potassium acetate). Activate with Yellow #5, $NaH_2PO_4$ and $Na_2HPO_4$ to adjust pH to approximately 7.60.

(3) 2.4% glutaraldehyde, 5% potassium acetate, 0.001% keyacid blue, 0.0025% Laureth-23, Q.S. to 100 ml distilled water (no isopropanol). Activate with Yellow #5, $NaH_2PO_4$ and $Na_2HPO_4$ to adjust pH to approximately 7.60.

(4) 2.4% glutaraldehyde, 15% isopropanol, 5% potassium acetate, 0.001% keyacid blue, 0.0025% Laureth-23, Q.S. to 100 ml distilled water. Activate with Yellow #5, $NaH_2PO_4$ and $Na_2HPO_4$ to adjust pH to approximately 7.60. Dilute 2+1 with synthetic hard water. (1.6% glutaraldehyde, 10% isopropanol, 3.33% potassium acetate).

Expose *M. bovis* var. BCG to Formulas (1)-(4)

Forty-five (45.0) ml of the chosen formula was put into a 250 ml Erlenmeyer flask and brought to temperature in a 20±1° C. water bath. Five (5.0) ml of *M. bovis* var. BCG suspension containing 5.0% (v/v) heat-inactivated calf serum were added and the solution was swirled to mix. After exposure times of 2.5, 5.0, 7.5, and 10.0 minutes at 20±1° C., 1.0 ml of the disinfectant/culture solution was removed and serial ten-fold dilutions were made as 1.0 ml into 9 ml portions of Dey-Engley neutralizing recovery medium containing 1% glycine. The dilutions were filtered through 0.45 μm membrane filters and rinsed with approximately 50 ml of sterile deionized water (SDIW). The filters were placed onto M7H9 agar in petri plates. The plates were incubated for 3-4 weeks at 35±2° C. inverted in an air-vented autoclave bag to minimize water evaporation and drying of plates during the long incubation period. *M. bovis* var. BCG colonies were counted and multiplied by the appropriate dilution factor to determine the number of colony forming units (CFU) in the reaction flask at various time points (S).

In the same manner as described above, CIDEX® Solution diluted to 1.5% glutaraldehyde was tested against *M. bovis* var. BCG using exposure times of 5, 10, 20, and 30 minutes at 25±1° C. The entire test was repeated.

Validation of Neutralization

Two serial ten-fold dilutions of test-strength disinfectant were made as 1.0 ml into 9 ml of neutralizing recovery medium. Each dilution tube was spiked with about 200 CFU of *M. bovis* var. BCG held in 1.0 ml of recovery broth. After 10 minutes at ambient temperature, the dilutions were filtered through 0.45 μm membrane filters and rinsed with about 50 ml of SDIW. The filters were placed onto M7H9 agar in petri plates.

For a comparative number, about 200 CFU of *M. bovis* var. BCG were added to two tubes of neutralizing recovery medium. After 10 minutes at ambient temperature, the solutions were filtered through 0.45 μm membrane filters and rinsed with about 50 ml of SDIW. The filters were placed onto M7H9 agar in petri plates.

Plates were incubated for 3-4 weeks in an air-vented autoclave bag at 35±2° C. Similar numbers on all plates validated neutralization of the disinfectant and phenol by the recovery process.

Determine the Original Number of *M. bovis* var. BCG in the Reaction Flask ($S_o$)

The test culture was assayed to determine the original number of CFU in the reaction flask. Five (5.0) ml of *M. bovis* var. BCG were added to 45 ml of SDIW and swirled to mix. One (1.0) ml was removed and serial ten-fold dilutions were made into 9 ml portions of neutralizing recovery medium. Three sets of dilutions were made. Dilutions 3 through 6 were filtered through 0.45 μm membrane filters and rinsed with approximately 50 ml of SDIW. The filters were placed onto M7H9 agar in petri plates and incubated for 4 to 5 weeks at 35±2° C. in an air-vented autoclave bag. The *M. bovis* var. *BCG* colonies were counted and multiplied by the appropriate dilution factor to determine the number of CFU originally in the reaction flask ($S_o$).

In both studies, undiluted formulations containing 2.4% glutaraldehyde, 15% isopropanol, and 5% potassium acetate, killed *M. bovis* var. BCG faster than all other formulas including CIDEX®. The same formula diluted 1.5-fold to approximately 1.6% glutaraldehyde, 10% isopropanol, and 3.33% potassium acetate had the second fastest kill of *M. bovis* var. BCG. The formula containing 2.4% glutaraldehyde and 15% isopropanol (no potassium acetate) killed *M. ovis* var. BCG slightly faster than the formula containing 2.4% glutaraldehyde and 5% potassium acetate (no isopropanol) and CIDEX®.

Example 3

This example shows a test to measure the relative concentrations of glutaraldehyde in the air above (vapors) for various glutaraldehyde (GA) test solutions.

Equal 1.0 L volumes of 1) 1.0, 2.0, and 2.5% GA in water, 2) 1.0, 2.0, and 2.5% GA plus 25% IPA in water, 3) CIDEX® Activated Dialdehyde Solution (2.5% GA), 4) the invention (3.0% GA+25% EPA plus 8% acetate), and 5) formulation IV (2.5% GA+20% IPA plus 8% acetate) were placed in the bottom of 5.0 gallon glass jugs. The jugs were stoppered, and the stoppers had two different sizes of glass tubes with the longer glass tube connected to an air pump, and the shorter glass tube connected to an airstone in a solution of MBTH. After 1.0 hour of air saturation, a constant volume of air was pumped through the headspace of the glass jug, caught in a solution of 50.0 ml of 0.5% 3-methyl-2-benzothiazolinone (MBTH), held for 5.0 minutes, 20.0 ml of 1.75% oxidant (Ferric chloride hexahydrate and sulfamic acid) was added, held for 1.0 hour, and the resulting color was measured for absorbance. The GA reacted with these solutions to turn various intensities of green/blue as a function of the concentration of GA. The measurements were compared directly and to a standard curve to determine the concentration of GA in the air (vapors) as released by the 1.0 L of various test solutions. The results showed fume suppression when acetate was present.

Glutaraldehyde vapors released from the formulations of the present invention where alcohol and acetate were present were consistently significantly lower than the CIDEX® solution. For example the glutaraldehyde vapors released from the formulation that was nominally 3% glutaraldehyde, 25% isopropanol alcohol and 8% potassium acetate and the formulation which was nominally 2.5% glutaraldehyde, 20% isopropanol alcohol and 8% potassium acetate are 65-80% and 78-85% lower than glutaraldehyde vapors released by CIDEX® (2.5% glutaraldehyde), respectively. This study, therefore demonstrates that there are much lower fumes of glutaraldehyde from the invention (glutaraldehyde+isopropanol+acetate salts) than from CIDEX® (glutaraldehyde only). Also there are similar levels of glutaraldehyde fumes from just glutaraldehyde vs glutaraldehyde+isopropanol. The conclusion is that acetate salts are somehow suppressing the fumes of glutaraldehyde.

The above data and the conclusions reached from it, make it clear that the invention accomplishes at least all of its stated primary objectives.

What is claimed is:

1. An aqueous, room temperature, low-fumes, disinfecting and/or sterilizing water-based solution having an activated pH of from 7.3 to about 7.9 comprising:

from about 2.0% to about 5.0% glutaraldehyde by volume;

from about 5.0% to about 26.0% alcohol by volume, wherein the alcohol is selected from the group consisting of methanol, ethanol, and isopropanol;

an effective amount of a buffer compatible with glutaraldehyde, wherein the buffer is phosphate buffer; and from about 3% by weight to about 8% by weight of an acetate salt.

2. An aqueous disinfecting and/or sterilizing solution according to claim 1 wherein the alcohol concentration is 24% to about 26% by volume.

3. An aqueous disinfecting and/or sterilizing solution according to claim 2 wherein the acetate salt is present at about 8% by weight of the total solution.

4. An aqueous disinfecting and/or sterilizing solution according to claim 1 further including a surfactant selected from the group consisting of nonionic, cationic and anionic surfactants at a level of from 0.0025% to 0.01% by weight.

5. An aqueous disinfecting and/or sterilizing solution according to claim 4 wherein the surfactant is a nonionic surfactant.

6. An aqueous disinfecting and/or sterilizing solution according to claim 1 wherein the solution comprises above 2% to about 5% by volume of glutaraldehyde.

7. A disinfectant kit comprising:

a first container of storable solution that is stable for up to 12 months containing:

from about 2% to about 5% by volume of glutaraldehyde;

from about 5% to about 26% by volume of alcohol wherein the alcohol is selected from the group consisting of methanol, ethanol, and isopropranol; and a sodium or potassium acetate salt of from about 3% by weight to about 8% by weight;

a second container of phosphate buffer in an amount sufficient to provide a concentration of 4 grams per liter to 7 grams per liter, and to provide a pH when combined with the first container of from 7.3 to 7.9; and instructions for mixing said storable solution and said phosphate buffer to provide a working disinfecting solution that is stable for up to 14 days.

8. A disinfectant kit according to claim 7, wherein the first container comprises above 2% to about 5% by volume of glutaraldehyde.

9. A disinfectant kit comprising:

a first container of storable solution that is stable for up to 12 months containing:

from about 2% to about 5% by volume of glutaraldehyde;

from 24% to about 26% by volume of alcohol wherein the alcohol is selected from the group consisting of methanol, ethanol, and isopropranol; and an acetate salt of about 8% by weight;

a second container of phosphate buffer in an amount sufficient to provide a concentration of 4 grams per liter to 7 grams per liter, and to provide a pH when combined with the storable solution of from 7.3 to 7.9; and instructions for mixing said storable solution and said phosphate buffer to provide a working disinfecting solution that is stable for up to 14 days.

10. A disinfectant kit according to claim 9, wherein the first container comprises above 2% to about 5% by volume of glutaraldehyde.

11. A method of enhancing kill and decreasing fumes of glutaraldehyde disinfectant water based solution, comprising:

mixing from about 2.0% to about 5.0% glutaraldehyde by volume;

from about 5.0% to about 26.0% alcohol by volume, wherein the alcohol is selected from the group consisting of methanol, ethanol, and isopropanol; and an effective amount of a buffer compatible with glutaraldehyde, wherein the buffer is phosphate buffer; with from about 3% by weight to about 8% by weight of an acetate salt, wherein the resultant mixture has an activated pH of from 7.3 to about 7.9.

* * * * *